US010524760B2

(12) United States Patent
Nagesh

(10) Patent No.: US 10,524,760 B2
(45) Date of Patent: Jan. 7, 2020

(54) X-RAY TUBE BEARING FAILURE PREDICTION USING DIGITAL TWIN ANALYTICS

(71) Applicant: General Electric Company, Schenectady, NY (US)

(72) Inventor: Shivaprasad Nagesh, Bangalore (IN)

(73) Assignee: General Electric Company, Schenectady, NY (US)

( * ) Notice: Subject to any disclaimer, the term of this patent is extended or adjusted under 35 U.S.C. 154(b) by 252 days.

(21) Appl. No.: 15/718,750

(22) Filed: Sep. 28, 2017

(65) Prior Publication Data

US 2019/0090840 A1    Mar. 28, 2019

(51) Int. Cl.
| A61B 6/00 | (2006.01) |
| G05B 23/02 | (2006.01) |
| A61B 6/03 | (2006.01) |
| A61B 6/10 | (2006.01) |
| H05G 1/54 | (2006.01) |

(52) U.S. Cl.
CPC .............. *A61B 6/586* (2013.01); *A61B 6/035* (2013.01); *A61B 6/102* (2013.01); *A61B 6/40* (2013.01); *G05B 23/0283* (2013.01); *H05G 1/54* (2013.01)

(58) Field of Classification Search
CPC .............. G05B 23/094; G05B 23/0283; G05B 23/0294
See application file for complete search history.

(56) References Cited

U.S. PATENT DOCUMENTS

| 2003/0139665 A1* | 7/2003 | Takayama | G16H 40/40 600/407 |
| 2005/0021373 A1* | 1/2005 | Spahn | A61B 6/00 705/2 |
| 2010/0030492 A1 | 2/2010 | Kar et al. | |
| 2014/0201571 A1* | 7/2014 | Hosek | G06F 11/2257 714/26 |
| 2017/0178311 A1* | 6/2017 | Pal | H04W 4/80 |

* cited by examiner

*Primary Examiner* — Yara B Green
(74) *Attorney, Agent, or Firm* — Hanley, Flight and Zimmerman, LLC

(57) ABSTRACT

Methods and apparatus for predicting x-ray tube liquid bearing failure are disclosed. An example circuit board device includes a sensor to detect, in a free run mode of an x-ray tube, vibration in an x-ray tube housing. The example device includes a digital signal processor to process vibration information representing vibration detected to generate x-ray tube characterization information. The example device includes a communication interface to relay the x-ray tube characterization information to a cloud infrastructure to process the characterization information to generate a failure prediction based on x-ray tube bearing coast down characteristics extracted from the characterization information. Other example instructions cause a machine to receive x-ray tube characterization information related to bearing vibration in the x-ray tube. The instructions, when executed, cause the machine to process the information based on coast down characteristics extracted from the information to identify a rate of failure and/or a time to failure, etc.

20 Claims, 17 Drawing Sheets

| Curve | Slope |
|---|---|
| Speed Free Run # | 5 |
| Speed Free Run # | 5.05 |
| Speed Free Run # | 5.3 |
| Speed Free Run # | 5.5 |
| Speed Free Run # | 6.5 |
| Speed Free Run # | 7.5 |
| Speed Free Run # | 10 |
| Speed Free Run # | 12.5 |

X-RAY TUBE BEARING FAILURE PREDICTION USING DIGITAL TWIN ANALYTICS

FIELD OF THE DISCLOSURE

This disclosure relates generally to bearing failure prediction, and, more particularly, to methods, systems, and apparatus for x-ray tube liquid metal bearing failure prediction using digital twin analytics.

BACKGROUND

In non-invasive imaging systems, x-ray tubes are used in various x-ray systems, such as computed tomography (CT) systems, as a source of ionizing (x-ray) radiation. The ionizing radiation is emitted from an x-ray tube in response to control signals during an examination or imaging sequence. An emitter within the cathode emits a stream of electrons in response to heat resulting from an applied electrical current, and/or an electric field resulting from an applied voltage to a properly shaped metallic plate in front of the emitter. The anode includes a target that is impacted by the stream of electrons. The target, as a result of impact by the electron beam, produces x-ray radiation to be emitted toward an imaged volume. In such imaging systems, a portion of the radiation passes through a subject of interest, such as a patient, baggage, or an article of manufacture, and impacts a digital detector or a photographic plate where the image data is collected. The signals are then processed to generate an image that may be displayed for review. Parts of the x-ray system, including the x-ray tube, deteriorate over time based on repeated use. Failure and/or other unacceptable degradation in use can occur unpredictably at inopportune times, resulting in a need to reobtain images and unnecessary x-ray exposure for patients, as well as wasted patient, radiologist, and x-ray technician time to arrange for a repeated scan. X-ray system downtime for repairs also negatively impacts healthcare facility scheduling, billing, and patient care.

BRIEF SUMMARY

Certain examples provide a circuit board device including a sensor to detect, in a free run mode of an x-ray tube, vibration in an x-ray tube housing. The example device also includes a digital signal processor to process vibration information representing the vibration detected by the sensor to generate x-ray tube characterization information. The example device further includes a communication interface to relay the x-ray tube characterization information to a cloud infrastructure to process the x-ray tube characterization information to generate a failure prediction based on x-ray tube bearing coast down characteristics extracted from the x-ray tube characterization information.

Certain examples provide a method including detecting, in a free run mode of an x-ray tube using a sensor, vibration in an x-ray tube housing. The method includes processing, using a digital signal processor, vibration information representing the vibration detected by the sensor to generate x-ray tube characterization information. The method includes relaying, via a communication interface, the x-ray tube characterization information to a cloud infrastructure to process the x-ray tube characterization information to generate a failure prediction based on x-ray tube bearing coast down characteristics extracted from the x-ray tube characterization information.

Certain examples provide a tangible computer readable storage medium comprising instructions. The instructions when executed, cause a machine to at least receive, from a circuit board on an x-ray tube, x-ray tube characterization information generated from vibration information detected by a sensor from an x-ray tube housing, the x-ray tube characterization information related to bearing vibration in the x-ray tube. The instructions when executed, cause the machine to at least process, using a processor, the x-ray tube characterization information based on x-ray tube bearing coast down characteristics extracted from the x-ray tube characterization information to identify at least one of a rate of failure or a time to failure. The instructions when executed, cause the machine to at least generate, using the processor, a failure prediction based on the at least one of a rate of failure or a time to failure. The instructions when executed, cause the machine to at least trigger, using the processor an alert based on the failure prediction.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
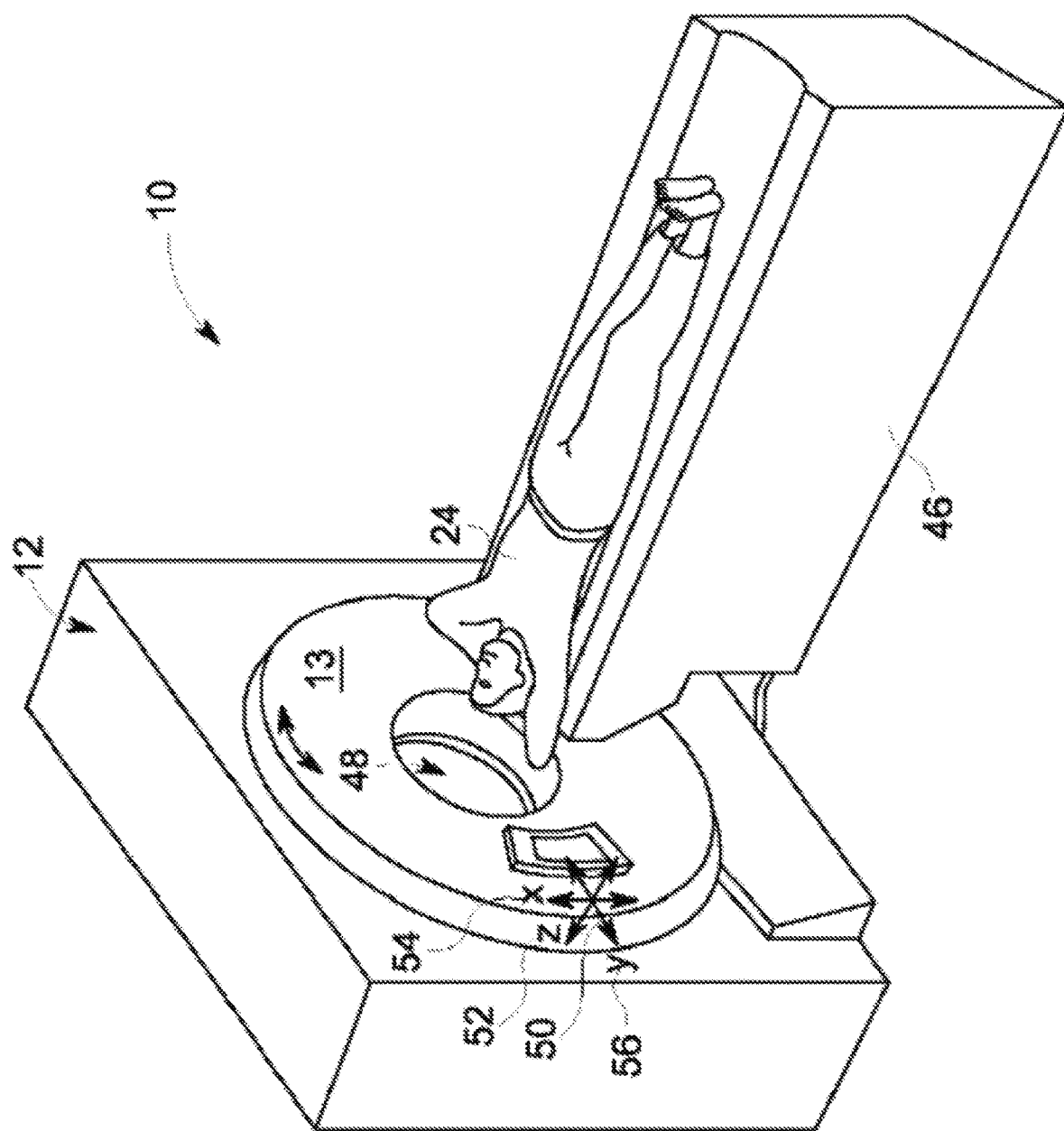
FIGS. 1-2 show an example computed tomography (CT) imaging system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

Certain examples provide systems and methods to predict bearing failure. Particularly, certain examples relate to liquid metal (LM) bearing failure prediction in an x-ray tube for an x-ray imaging system. In certain examples, a single board computer gathers data from the x-ray tube regarding x-ray tube operation, movement, and/or other bearing status, and transmits the data to a cloud-based system. A predictor running on the cloud-based system and/or an edge device generates a prediction of a rate and/or other timing of bearing failure, for example.

For example, when a free run command is given to make rotors coast down to zero naturally in an x-ray tube, the computer is triggered to periodically track an associated frequency. A digital single processor associated with the computer executes an algorithm to process periodically gathered data points and push the data to the cloud-based system. A function including an y/x slope determines decrease in rotor speed with respect to time. The cloud-based system combines multiple such functions to determine how bearing friction varies over time.

As the x-ray tube ages, the rate of fail frequency increases. In certain examples, a learning model in the cloud-based system extrapolates from the function information to produce a non-linear transfer function which models the rate of fail frequency for the LM bearing of an x-ray tube. Using the model, a slope can be identified in the function of the data which provides a prediction of how much time (e.g., hours, minutes, second, etc.) is left before the bearing fails.

Thus, impending failure of a liquid metal bearing tube can be identified and repaired or replaced in advance, rather than at the point of failure. LM bearing tubes are expensive, costing hospitals $45,000-$50,000 to purchase and $100,000 s to replace, so being able to proactively order and schedule a replacement is much preferable to forced replacement after the bearing has failed.

Rather than unplanned downtime, replacement of the tube can occur during planned downtown. Connecting a sensor and processor to the x-ray tube and connecting the processor with algorithms running on extracted data in the cloud and/or on an edge device is challenging but enables analytics for better prediction and outcome for the x-ray imaging system.

Additionally, in certain examples, an interactive interface can be provided to schedule downtime for x-ray tube replacement/repair. In certain examples, an indication can be provided to a field engineer, service team, etc., from the cloud-based system when a rate and/or time of bearing failure has been determined. For example, a rule can be set to notify a technician regarding x-ray tubes that have been predicted to fail in the next ten days, etc. An authorized person, device, system, and/or monitoring application can receive such messages to check for further information, check stock, plan for replacement, etc. The advance prediction of the failure helps to reduce the inventory cost for service and plan proactive service visit to hospital for an about-to-fail part replacement. This helps to reduce the downtime of the medical device and upholds the customer satisfaction.

In operation, a "coast down" measurement acquisition is conducted using cloud-based analytics and/or an edge device using a digital twin of the x-ray tube and LM bearing based on data obtained from the sensor on the tube. When the tube is activated with a free run command, data acquisition begins. Periodic measurement is obtained in the time domain and is converted into the frequency domain to determine the peak frequency by running a time to frequency domain analysis such as a Fast Fourier Transform (FFT), etc. The peak frequency forms an output signal that is relayed to the cloud using cloud connectivity.

Analytics software running in the cloud builds the coast down characteristics of the x-ray tube with respect to time and measures a slope of coast down for the x-ray tube and its liquid metal bearing, for example. Such information can be gathered and determined for a plurality of coast downs, and resulting curves are overlapped to show how the x-ray tube is performing. The slope of the curve is an indication of the friction of the bearing. The coast down characteristic is the measurement of time taken for the speed to fall from "Y1" frequency @ "X1" time to "Y2" frequency @ "X2" time. The slope can be calculated using simple formula like slope=$(Y2-Y1)/(X2-X1)$.

When the x-ray tube is new, the friction is low and the slope is small. For example, the time taken for the motor to coast down is very long when the x-ray tube and its bearing are new. As the x-ray tube ages, the coast down time becomes smaller, which indicates the wearing out of the bearing. The algorithm in the cloud predicts a time to fail by calculating the slope over many free run cycles, for example.

Each time a coast down curve is computed, the algorithm in the cloud-based system also measures the time between the slope change. A slope of rotor speed over time (V/S) is computed by actively learning from every coast down curve. Each time a coast down is computed, the algorithm in the cloud-based system knows the residual life from the cumulative damage model. Cumulative damage models are built from the information gathered on the x-ray tube. Based on a limit (e.g., set by the user, application, hardware configuration, etc.), automatic alerts are sent to indicate the potential time to fail for the particular x-ray tube and LM bearing.

The systems and methods described herein have many commercial advantages. For example, as the x-ray tube failure is predicted in advance, replacement tube stock at an associated service location will come down significantly, leading to reduced inventory. As the failure is predicted in advance, a preventive maintenance schedule can be set with the customer to reduce the down time significantly and increasing the customer satisfaction. As the performance of the LM bearing is monitored in near real time, engineering fixes and product updates have access to asset information with the corresponding insights, which helps to evaluate the applicability of the fix with a large population size, for example.

Thus, while LM bearing x-ray tubes are characterized by long service life, low noise, and being expensive to buy, certain examples facilitate improved monitoring, maintenance, and scheduling of LM bearing x-ray tubes when they start to fail and/or are otherwise nearing failure. A prediction and/or other forecast of impending rotor LM bearing failure for the x-ray tube helps to improve x-ray system operation, reliability, customer satisfaction, and management of inventory, for example. Using a sensor network, cloud computing, and digital twin analytics, performance of the LM bearing in an x-ray tube can be monitored and managed for improved uptime and performance, for example.

Figure 2:
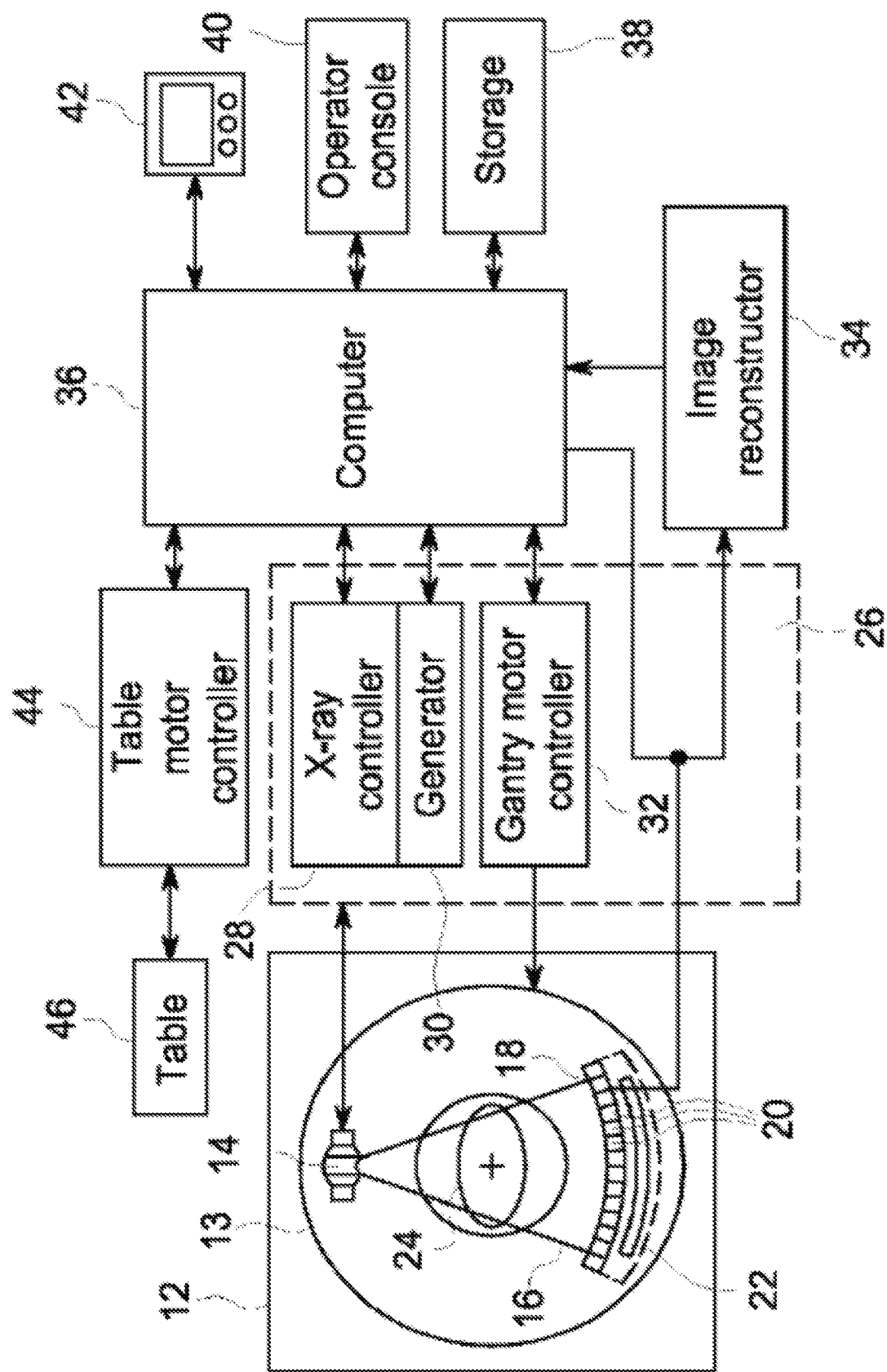

Turning to the figures, FIGS. 1 and 2 show a computed tomography (CT) imaging system 10 including a gantry 12. Gantry 12 has a rotary member 13 with an x-ray source 14 (e.g., an x-ray tube) that projects a beam of x-rays 16 toward a detector assembly 18 on the opposite side of the rotary member 13. A main bearing may be utilized to attach the rotary member 13 to the stationary structure of the gantry 12. The x-ray source 14 includes either a stationary target or a rotating target. The detector assembly 18 is formed by a plurality of detectors 20 and data acquisition systems (DAS) 22, and can include a collimator. The plurality of detectors 20 sense the projected x-rays that pass through a subject 24, and the DAS 22 converts the data to digital signals for subsequent processing. Each detector 20 produces an analog or digital electrical signal that represents the intensity of an impinging x-ray beam and hence the attenuated beam as it passes through a subject 24. During a scan to acquire x-ray projection data, the rotary member 13 and the components mounted thereon can rotate about a center of rotation.

Rotation of the rotary member 13 and operation of the x-ray source 14 are governed by a control mechanism 26 of the CT system 10. The control mechanism 26 can include an x-ray controller 28 and a generator 30 that provides power and timing signals to the x-ray source 14 and a gantry motor controller 32 that controls the rotational speed and position of the rotary member 13. An image reconstructor 34 receives sampled and digitized x-ray data from the DAS 22 and performs high speed image reconstruction. The reconstructed image is output to a computer 36 which stores the image in a computer storage device 38.

The computer 36 also receives commands and scanning parameters from an operator via an operator console 40 that has some form of operator interface, such as a keyboard, mouse, touch sensitive controller, voice activated controller, or any other suitable input apparatus. A display 42 allows the operator to observe the reconstructed image and other data from the computer 36. The operator supplied commands and parameters are used by the computer 36 to provide control signals and information to the DAS 22, the x-ray controller 28, and the gantry motor controller 32. In addition, the computer 36 operates a table motor controller 44 which controls a motorized table 46 to position the subject 24 and the gantry 12. Particularly, the table 46 moves a subject 24 through a gantry opening 48, or bore, in whole or in part. A coordinate system 50 defines a patient or Z-axis 52 along which the subject 24 is moved in and out of the opening 48, a gantry circumferential or X-axis 54 along which detector assembly 18 passes, and a Y-axis 56 that passes along a direction from a focal spot of the x-ray tube 14 to the detector assembly 18.

Figure 3:
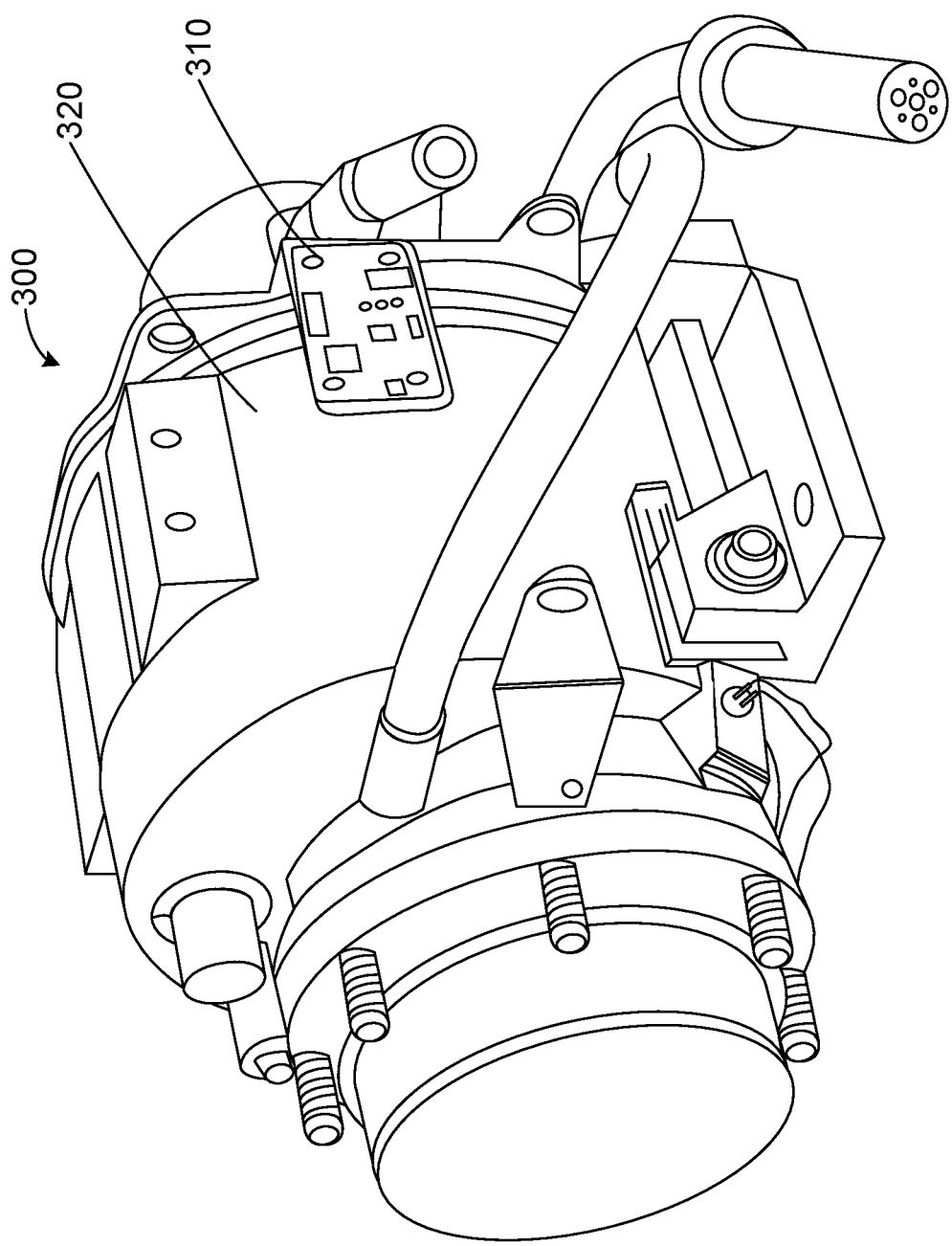
FIG. 3 illustrates an example x-ray tube that can form and/or be used in the x-ray source of the example of FIGS. 1-2.

FIG. 3 illustrates an example x-ray tube 300 that can form and/or be used in the x-ray source 14 of the example of FIGS. 1-2. The example x-ray tube 300 includes a sensor-enabled data acquisition circuit board 310 mounted on a tube casing 320. The example board 310 includes one or more sensors, such as an accelerometer, potentiometer, encoder, etc., connected to a digital signal processor (DSP) or digital signal controller on the board 310. One or more signal processing algorithms can be stored on and/or executed by the DSP to evaluate gathered sensor data. A communication component, such as wireless cloud connectivity (e.g., via Wi-Fi, cellular, etc.), etc., can relay processed data from the DSP to a cloud infrastructure for further processing of data off chip 310 and leveraging the greater resources of the cloud infrastructure, for example. For example, the cloud infrastructure can be leveraged to provide data analytics, business analytics, alerts/messaging, field operation/maintenance, etc., based on data acquired by the sensor(s), processed by the processor, and communicated to the cloud via the board 310 on the tube 300.

Figure 4:
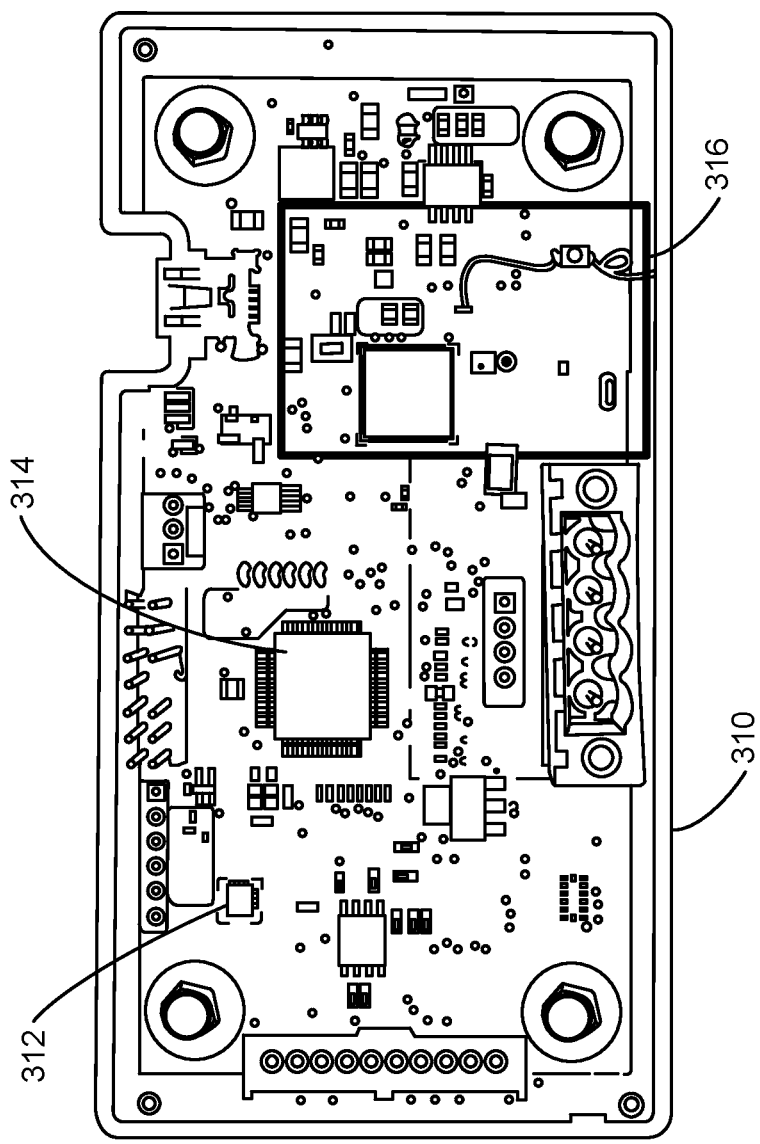
FIGS. 4-5 illustrate example implementations of the sensor-enabled data acquisition circuit board of FIG. 3.

FIG. 4 illustrates an example implementation of the sensor-enabled data acquisition circuit board 310. In the example of FIG. 4, the board 310 includes one or more sensors, such as an accelerometer 312. The sensor(s) 312 can monitor activity and/or other environmental factor(s) with respect to the x-ray tube 300 and its tube casing 320 (also referred to as x-ray tube characterization information), such as vibration in the tubing casing 320, etc. The board 310 also includes a controller, such as a DSP 314, to process data from the sensor(s) 312. The board 310 further includes a communication interface 316, such as for cloud connectivity via Wi-Fi, cellular, near field communication (NFC), and/or other wireless/wired communication interface. Using the board 310, sensors 312 can be integrated on the X-ray tube 300 and provide input to signal processing algorithm(s) running on the digital signal controller 314, while providing connectivity of the algorithm's output to the cloud in near real time (e.g., accounting for processing, transmission, and/or storage latency, etc.) via the communication interface 316. Thus, for example, the sensor(s) 312 can provide vibration information and/or other x-ray tube characterization information to the DSP 314, which can extract frequency information from the vibration data and provide the frequency information to the cloud to extrapolate friction information with respect to an x-ray bearing, etc.

Figure 5:
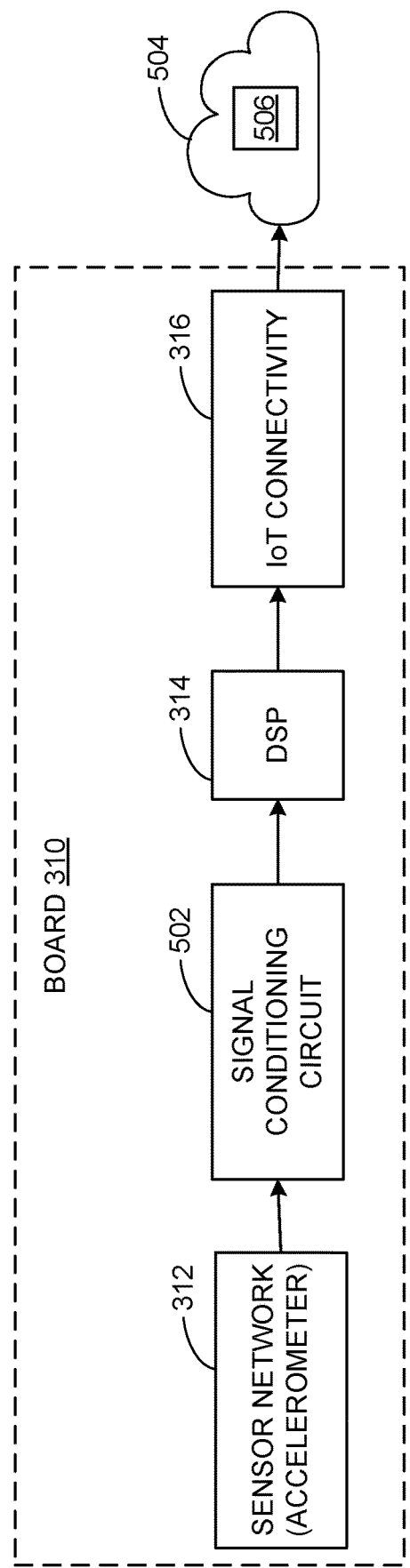

FIG. 5 illustrates another representation or view of components of the example board 310 of FIG. 4. As shown in the example of FIG. 5, the sensor network (e.g., accelerometer, etc.) 312 provides data collection to a signal conditioning circuit 502 to preprocess and/or otherwise "clean up" obtained sensor data for processing by the DSP 314. The signal conditioning circuit 502 removes noise from the output of the sensor network 312, which includes signals of large bandwidth (e.g., big frequency band, etc.) as well as noise acquired during measurements, etc. The signal conditioning circuit 502 also selects one or more frequencies of interest to compute tube rotor coast down. For example, if the signal provided by the sensor(s) 312 has a bandwidth of 0 to 500 Hz, and the tube rotor spins at 140 Hz, the signal conditioning circuit 504 removes frequencies above 150 Hz and provides signal data from 0-150 Hz to the DSP 314.

Thus, the sensor network 312 detects a vibration signature from the tube casing or housing 320, which can be conditioned and/or otherwise preprocessed (e.g., to amplify the signal, reduce noise, filter the signal, etc.) for further processing by the DSP 314. The DSP 314 can process the acquired signal data to provide windowing, Fast Fourier Transform (FFT), cognitive computing analysis, communication, etc. Vibration in the x-ray tube casing 320 can be indicative of impending bearing failure and/or other tube 300 damage, defect, wear, etc.

In the example of FIG. 5, the DSP 314 applies digital signal processing to the input signal data to derive peak frequency information from a time domain signal such as a Fast Fourier Transform (FFT), for example. For example, a coast down measurement can be acquired using the board 310 to trigger acquisition by the sensor network 312 when a free run ("F") command is issued over a controller area network (CAN) bus on the board 310. The command can be generated by the DSP 314 and/or other controller/processor on the board 310 and/or relayed from a cloud infrastructure 504 via the communication interface and/or other connectivity (e.g., Internet-of-Things or IoT connectivity, etc.) 316, for example.

In the example of FIG. 5, the cloud infrastructure 504 can analyze the processed measurement data to evaluate x-ray tube 300 coast down frequency over time. The cloud infrastructure 504 and/or an edge device between the board 310 and the cloud 504 can include a predictor 506 to build a cumulative damage model over time from the processed measurement data gathered from the board 310, and the cumulative damage model can be compared to a threshold or limit (e.g., set by a user, established from historical and/or modeled failure data, predicted via a digital twin, etc.). Once the cumulative damage model of the x-ray tube 300 (e.g., the liquid metal bearing(s) of the x-ray tube 300) meets or exceeds the threshold, an alert, alarm, warning, message, shutoff command, etc., is/are generated to indicate an impending failure, potential time to failure, etc.

Figure 6:
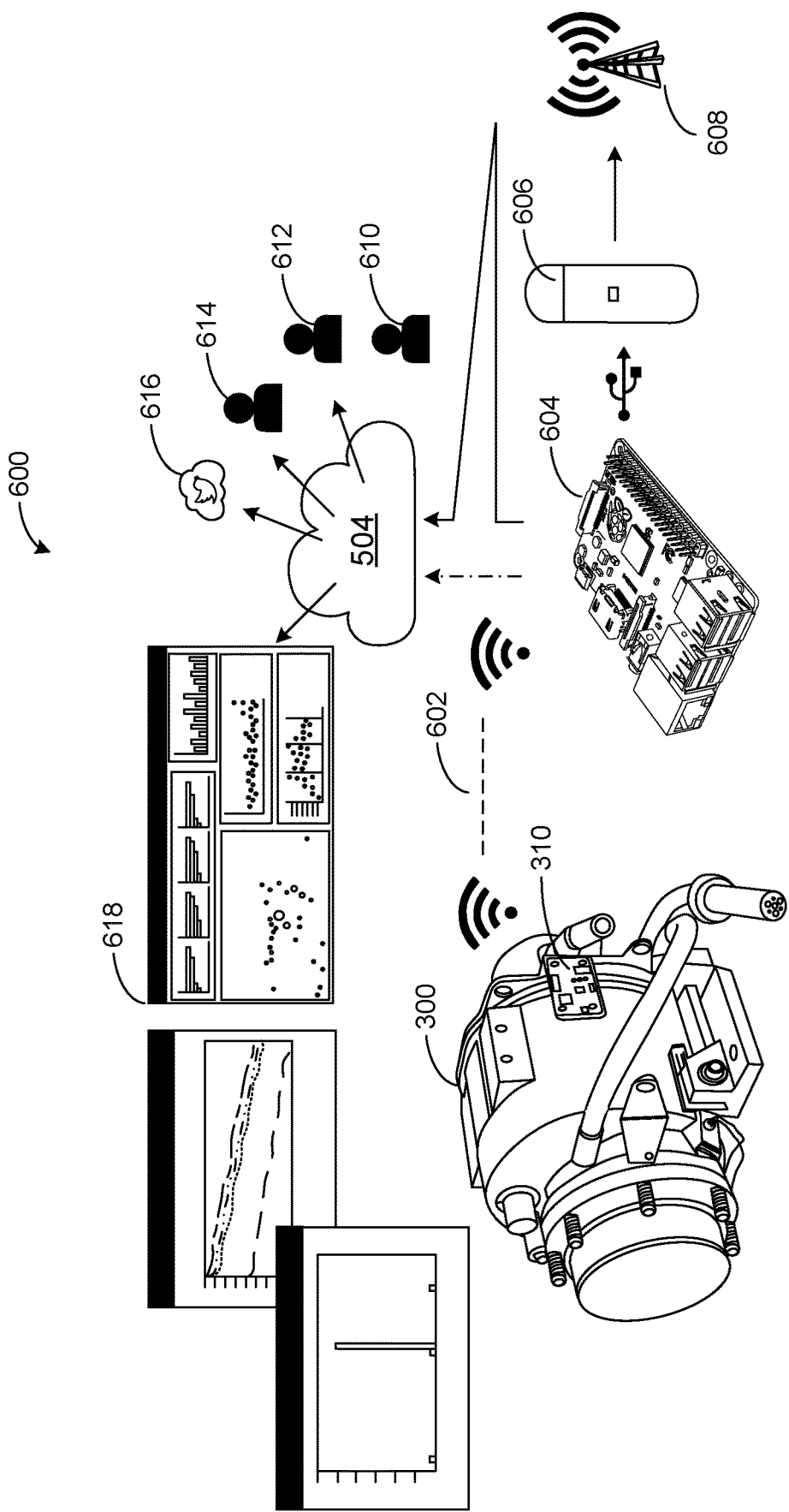
FIG. 6 illustrates an example x-ray tube monitoring ecosystem.

FIG. 6 illustrates an example monitoring ecosystem 600 in which the x-ray tube 300 and circuit board 310 communicate via a wireless channel 602 (e.g., Wi-Fi, etc.) with the cloud infrastructure 504, directly and/or via one or more other devices, such as a single board computer 604 (e.g., a Raspberry Pi, Arduino, etc.) with a communication interface 606 (e.g. a 3G data card, etc.) providing access to a cellular network 608. Data gathered and processed via the cloud 504 can then be provided to one or more outputs such as field operations 610, data science 612, business analysis 614, messaging/announcement 616, dashboard 618, etc.

Figure 7:
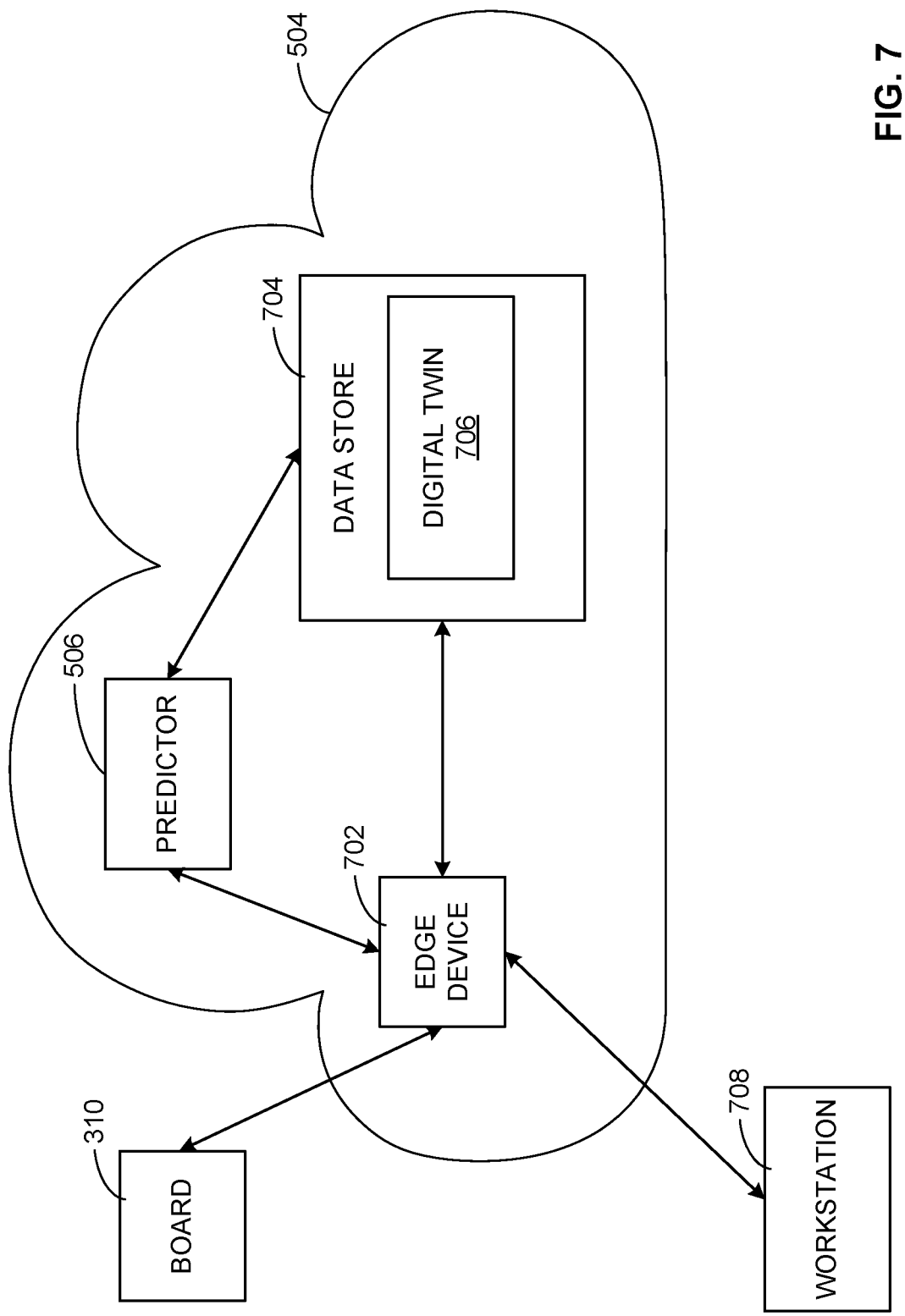
FIG. 7 illustrates an example implementation of the cloud infrastructure of FIGS. 5-7.

FIG. 7 illustrates an example implementation of the cloud infrastructure 504. As shown in the example of FIG. 7, the board 310 communicates with an edge device 702 in and/or near the cloud 504, which facilitates exchange of data with respect to the cloud infrastructure 504. The edge device 702 provides information to a data store 704, which includes a digital twin 706 representing and/or otherwise modeling the x-ray tube 300, for example. Thus, data gathered by the sensor(s) 312 and processed by the DSP 314 can be provided to the cloud 504 and stored in the data store 704 including being modeled by the digital twin 706, for example. The cloud infrastructure 504 also include the predictor 506, which processes the data to update the digital twin 706 and generate a prediction of x-ray tube 300 bearing failure (e.g., an estimated time of failure, time to failure, rate of decay/failure, etc.). The predictor 506 can alert a user, system, application, and/or other device to the failure prediction via a workstation 708, the board 310, etc. In certain examples, data from the board 310 representing peak frequency information from the x-ray tube 300 rotor, bearing, etc., can be plotted by the predictor 506 as one or more curves, and the curves can be overlaid to generate and/or update the digital twin 706. Based on the model of the digital twin 706 (e.g., include a failure threshold, historical failure/wear data, etc.), the predictor 506 can analyze the modeled set of curves to determine current x-ray tube 300 wear state and predict a time, rate, etc., of failure for the tube 300 (e.g., for the LM bearing, rotor, etc., of the x-ray tube 300).

Figure 8:
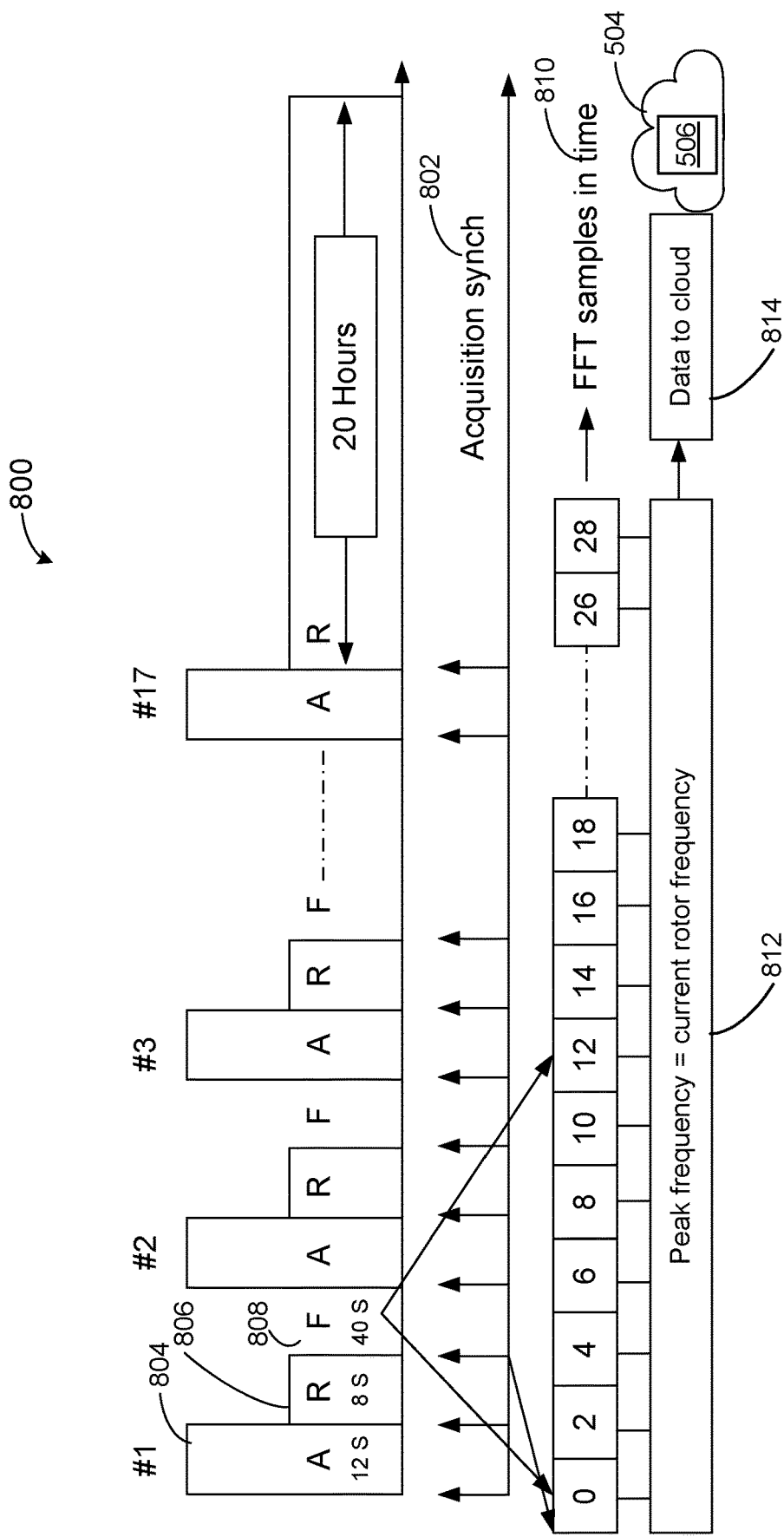
FIG. 8 illustrates an example free run or coast down measurement acquisition for an x-ray tube.

FIG. 8 illustrates an example free run or coast down measurement acquisition 800 using the board 310 and the cloud infrastructure 504. The DSP 314 tracks the commands that it receives from the system console and/or an external controller for a "free run command" 802 to the x-ray tube 300 on the sensor board 310 (e.g., a CAN command and/or other acquisition synch to disengage for free run or coast down operation of the x-ray tube 300). The command 802 triggers the sensor network 312 to detect a vibration signature from the x-ray tube casing 320 during the free run or coast down period.

As shown in the example acquisition 800 of FIG. 8, the x-ray tube cycles through an acceleration cycle (A) 804, gets into a run phase (R) 806, and a free run (F) 808, triggered by receipt of the free run command 802. When the tube is applied with the free run "F" period 808 based on a command 802 issued from the CAN bus, the sensor network 312 starts data acquisition. Acquired vibrational data from the sensor(s) 312 is preprocessed by the signal conditioning circuit 502, and hardware, firmware, and/or software inside the DSP 314 applies digital signal processing to derive peak frequency information from time domain signal information such as FFT, etc. As shown in the example of FIG. 8, the sensor network 312 obtains periodic measurement (e.g., samples) 810 in the time domain, and the DSP 314 generates peak frequency information 812 from the time domain signal by running a time-to-frequency domain analysis (e.g., FFT, etc.) on the acquired vibration time domain signal information. This output signal is then relayed 814 to the cloud 504 using cloud connectivity 316, for example. The predictor 506 evaluates the output signal to determine a prediction of tube bearing failure, rate of failure, etc.

While example implementations of the x-ray tube 14, 300 and associated components 504, 600 are illustrated in conjunction with FIGS. 1-8, processes and/or devices illustrated in conjunction with FIGS. 1-8 can be combined, divided, re-arranged, omitted, eliminated and/or implemented in any other way. Further, the example board 310, sensor(s) 312, DSP 314, communication interface 316, signal conditioning circuit 502, cloud infrastructure 504, single board computer 604, communication interface 606, etc. of FIGS. 1-8 can be implemented by hardware, machine readable instructions, software, firmware and/or any combination of hardware, machine readable instructions, software and/or firmware. Thus, for example, any of the example board 310, sensor(s) 312, DSP 314, communication interface 316, signal conditioning circuit 502, cloud infrastructure 504, single board computer 604, communication interface 606, etc., of FIGS. 1-8 can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example board 310, sensor(s) 312, DSP 314, communication interface 316, signal conditioning circuit 502, cloud infrastructure 504, predictor 506, single board computer 604, communication interface 606, etc., of FIGS. 1-8 is/are hereby expressly defined to include a tangible computer readable storage device or storage disk such as a memory, a digital versatile disk (DVD), a compact disk (CD), a Blu-ray disk, etc. storing the software and/or firmware. Further still, the example board 310 can include elements, processes and/or devices in addition to, or instead of, those illustrated in conjunction with FIGS. 1-8, and/or may include more than one of any or all of the illustrated elements, processes and devices.

Flowcharts representative of example machine readable instructions for implementing the example board 310, algorithms executing on or with respect to the example 310, and/or other components/processes of FIGS. 1-8 are shown in conjunction with FIGS. 9-12. Further, although the example program is described with reference to the flowcharts illustrated in conjunction with FIGS. 9-12, many other methods can alternatively be used. For example, the order of execution of the blocks may be changed, and/or some of the blocks described may be changed, eliminated, or combined. Although the flowcharts of FIGS. 9-12 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of FIGS. 9-12 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 9-12 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 9:
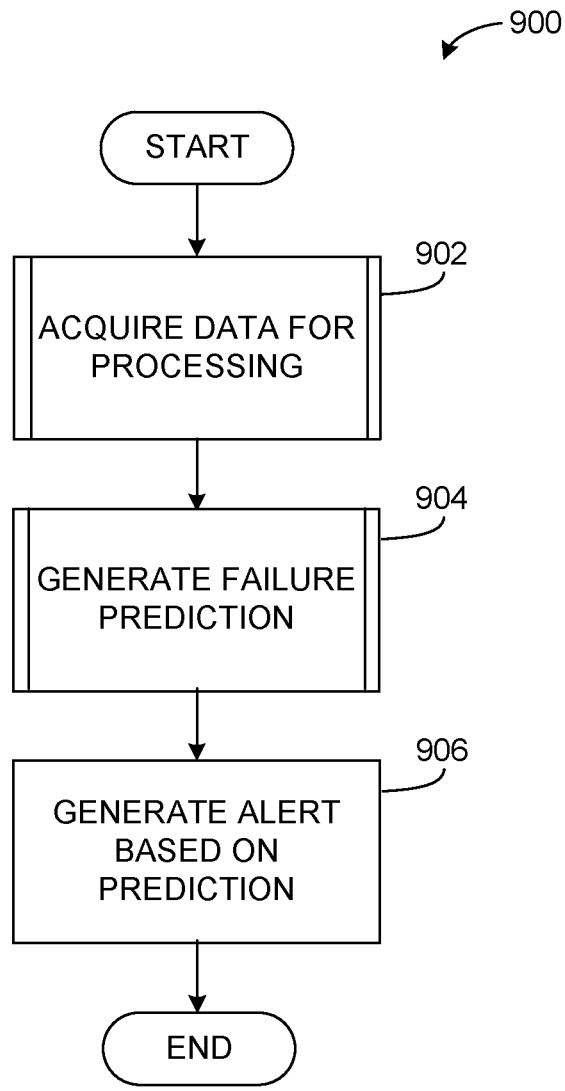
FIGS. 9-12 illustrate flow diagrams for example methods to generate a prediction for x-ray tube failure.

FIG. 9 is a flow diagram of an example method 900 representative of example machine readable instructions that can be executed by the board 310 (e.g., the DSP 314, signal conditioning circuit 502), cloud 504, etc., to generate a prediction for x-ray tube failure.

At block 902, x-ray tube 300 measurement data is acquired for processing. For example, the single board computer 310 gathers data from the x-ray tube 14, 300 for the x-ray imaging system 10 to predict bearing failure (e.g., LM bearing failure, etc.) in the tube 14, 300. In certain examples, the board 310 gathers data from the x-ray tube 14, 300 regarding x-ray tube 14, 300 operation, movement, and/or other bearing status, and transmits the data to the cloud-based system 504 for further processing and analytics such as to generate a prediction of failure.

For example, when a free run command 802 is given to the x-ray tube 300, the computer in 310 is triggered to periodically track the frequency of the tube rotor. The digital signal processor 314 associated with the computer executes an algorithm to process periodically gathered data points and push the data to the cloud-based system 504. A function including an y/x slope determines decrease in rotor speed with respect to time, for example. The cloud-based system 504 combines multiple such functions to determine how bearing friction varies over time, for example.

In operation, a "coast down" measurement acquisition is conducted using cloud-based analytics and/or an edge device using a digital twin of the x-ray tube 300 and LM bearing based on data obtained from the sensor 310 on the tube 300. When the tube 300 is activated with a free run command 802, data acquisition begins. Periodic measurement is obtained in the time domain, and a peak frequency is determined from the time domain signal by running a time to frequency domain analysis such as a Fast Fourier Transform (FFT), etc. The peak frequency forms an output signal that is relayed to the cloud 504 using cloud connectivity 316.

At block 904, the acquired x-ray tube measurement data is sent to the cloud infrastructure 504 to generate a tube failure prediction. For example, the predictor 506 running on the cloud-based system 504 and/or an edge device generates a prediction of a rate and/or other timing of bearing failure, for example.

As the x-ray tube ages, the rate of fail frequency increases. In certain examples, a learning model running on the predictor 506 in the cloud-based system 504 extrapolates from the function information provided by the board 310 to produce a non-linear transfer function which models the rate of fail frequency for the LM bearing of the x-ray tube 300. Using the model, a slope can be identified in the function of the data which provides a prediction of how much time (e.g., hours, minutes, second, etc.) is left before the bearing fails.

Analytics software running in the cloud 504 builds the coast down characteristics of the x-ray tube 300 with respect to time and measures a slope of coast down for the x-ray tube 300 and its liquid metal bearing, for example. Such information can be gathered and determined for a plurality of coast downs, and resulting curves are overlapped to show how the x-ray tube 300 is performing. The slope of the curve is an indication of the friction of the bearing. The coast down characteristic is the measurement of time taken for the speed to fall from "Y1" frequency at "X1" time to "Y2" frequency at "X2" time. The slope can be calculated by the predictor 506 using a formula such as slope=(Y2−Y1)/(X2−X1) (Equation 1), for example.

When the x-ray tube 310 is new, the friction is low and the slope is small. For example, the time taken for an x-ray tube motor to coast down is very long when the x-ray tube 310 and its bearing are new. As the x-ray tube 310 ages, the coast down time becomes smaller, which indicates the wearing out of the bearing. The algorithm of Equation 1 executed by the predictor 506 in the cloud 504 predicts a time to fail by calculating the slope over a plurality of free run cycles, for example.

Each time a coast down curve is computed, the predictor 504 in the cloud-based system 504 also measures a time between slope changes. A slope of rotor speed over time (V/S) is computed by actively learning from each coast down curve. Each time a coast down is computed, the algorithm in the cloud-based system 504 determines a residual life of the bearing based on the cumulative damage model. Cumulative damage models are built from the information gathered on the x-ray tube 300 by the board computer 310.

At block 906, an alert is generated based on the tube failure prediction. For example, based on a limit (e.g., set by the user, application, hardware configuration, etc.), automatic alerts are sent to indicate the potential time to fail for the particular x-ray tube 300 and LM bearing. Thus, impending failure of a liquid metal bearing tube 300 can be identified and repaired or replaced in advance, rather than at the point of failure. LM bearing tubes 300 are expensive, costing hospitals $45,000-$50,000 to purchase and $100,000 s to replace, so being able to proactively order and schedule a replacement is much preferable to forced replacement after the bearing has failed. Rather than unplanned downtime, replacement of the tube 300 can occur during planned downtown. Connecting the sensor 312 and processor 310 to the x-ray tube 300 and connecting the processor 310 with algorithms running on extracted data in the cloud 504 and/or on an edge device is challenging but enables analytics for better prediction and outcome for the x-ray imaging system.

Additionally, in certain examples, an interactive interface can be provided to schedule downtime for x-ray tube replacement/repair. In certain examples, an indication can be provided to a field engineer, service team, etc., from the cloud-based system when a rate and/or time of bearing failure has been determined. For example, a rule can be set to notify a technician regarding x-ray tubes that have been predicted to fail in the next ten days, etc. An authorized person, device, system, and/or monitoring application can receive such messages to check for further information, check stock, plan for replacement, etc. The advance prediction of the failure helps to reduce the inventory cost for service and plan proactive service visit to hospital for an about-to-fail part replacement. This helps to reduce the downtime of the medical device and upholds the customer satisfaction.

The systems and methods described herein have many commercial advantages. For example, as the x-ray tube failure is predicted in advance, replacement tube stock at an associated service location will come down significantly, leading to reduced inventory. As the failure is predicted in advance, a preventive maintenance schedule can be set with the customer to reduce the down time significantly and increasing the customer satisfaction. As the performance of the LM bearing is monitored in near real time, engineering fixes and product updates have access to asset information with the corresponding insights, which helps to evaluate the applicability of the fix with a large population size, for example.

Thus, while LM bearing x-ray tubes are characterized by long service life, low noise, and being expensive to buy, certain examples facilitate improved monitoring, maintenance, and scheduling of LM bearing x-ray tubes when they start to fail and/or are otherwise nearing failure. A prediction and/or other forecast of impending rotor LM bearing failure for the x-ray tube helps to improve x-ray system operation, reliability, customer satisfaction, and management of inventory, for example. Using a sensor network, cloud computing, and digital twin analytics, performance of the LM bearing in an x-ray tube can be monitored and managed for improved uptime and performance, for example.

Figure 10:
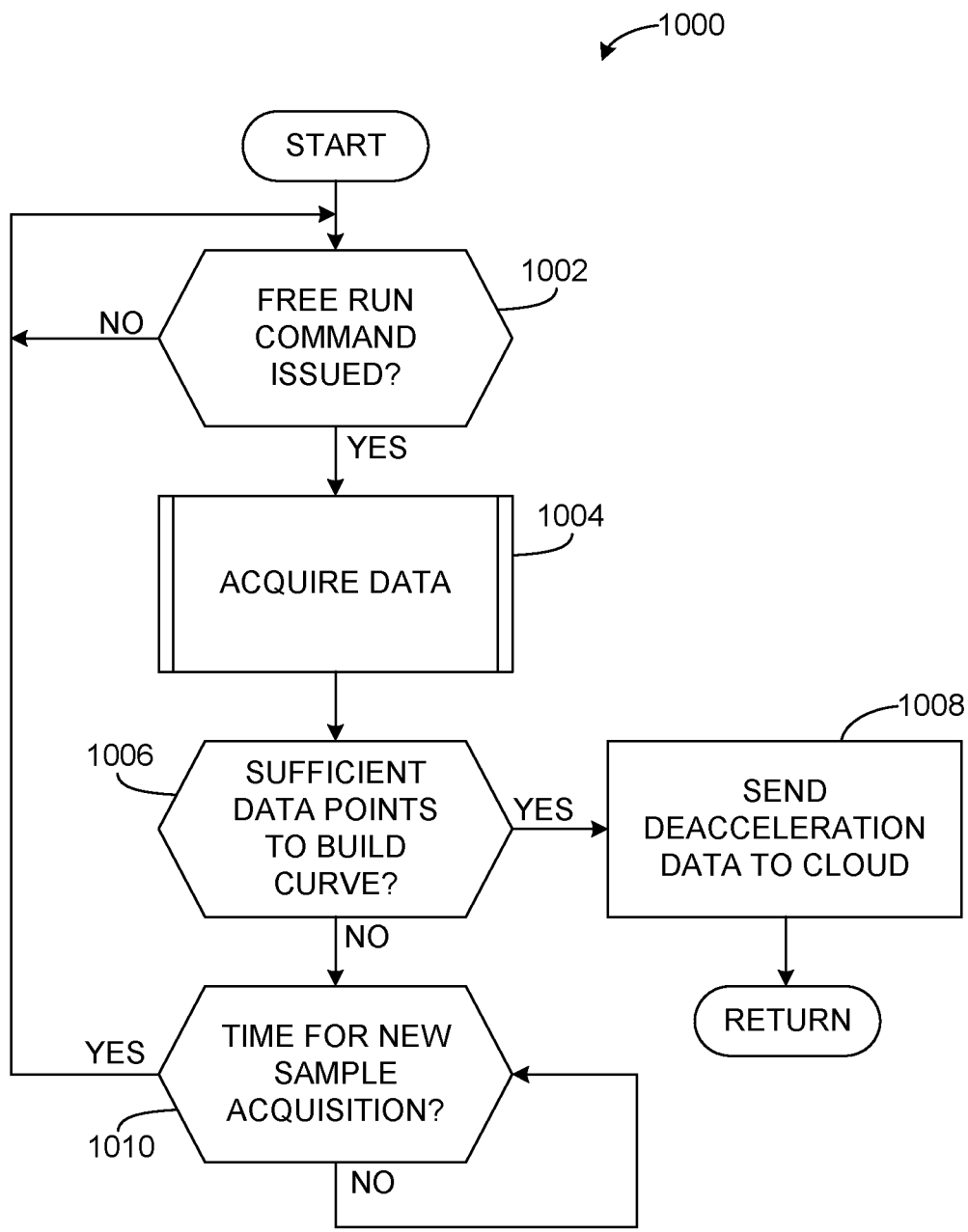

FIG. 10 illustrates further details regarding an example acquisition of data for processing (block 902 of the example of FIG. 9). At block 1002, commands 802 are evaluated to determine whether a free run or coast down command has been issued. When a free run/coast down command is detected by the board 310 to be issued, then, at block 1004, data is acquired from the sensor network 312 for the x-ray tube 300 via its casing 320. Thus, when the command 802 is issued to free run/coast, the sensor(s) 312 obtain data and the board 310 starts tracking a frequency of coast down. For example, every two seconds (e.g., 2, 4, 6, . . . , 28 seconds, etc.), the DSP 314 tracks frequency of rotor based on input from the sensor(s) 312 (e.g., as preprocessed and/or otherwise cleaned by the signal conditioning circuit 502, etc.).

The DSP 314 processes the data points (e.g., using FFT, etc.), and, at block 1006, evaluates whether enough data points have been gathered to form a curve to be analyzed by the cloud infrastructure 504. If enough frequency data points have been gathered to form a curve for analysis, then, at block 1008, the data is sent to the cloud infrastructure 504 for analysis. Control then reverts to block 904 to generate a failure prediction via the cloud infrastructure 504.

If insufficient data has been collected, then, at block 1010, the process waits for a new sample acquisition (e.g., after 2 seconds, 1 second, 5 seconds, 10 seconds, trigger, etc.). Then, once it is time for a new sample acquisition, the example process reverts to block 1002 to await another free run command.

Figure 11:
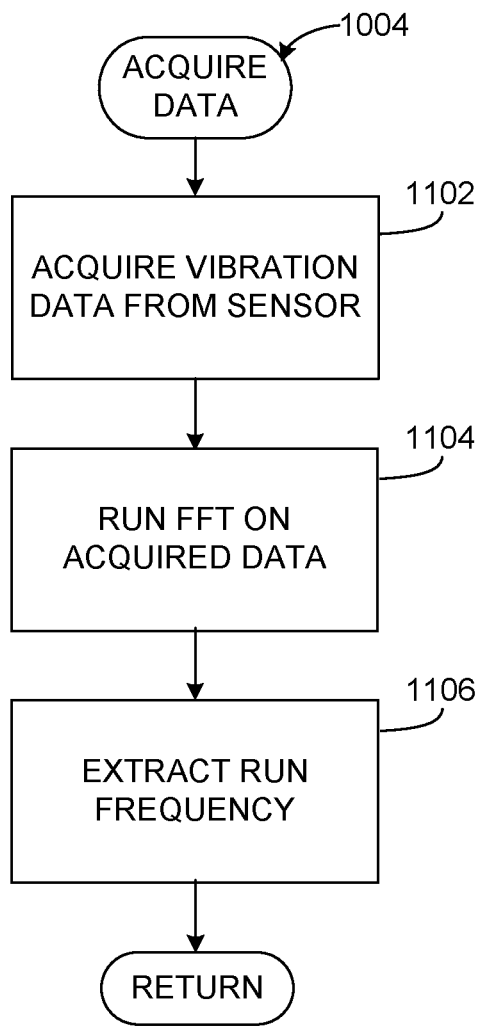

FIG. 11 illustrates further details regarding an example acquisition of data for processing (block 1004 of the example of FIG. 10). At block 1102, vibration data is acquired from the sensor(s) 312. For example, vibration data from rotor/bearing can be detected through the casing 320 by the sensor(s) 312. At block 1104, the gathered data is processed, such as by performing FFT analysis on the vibration data via the DSP 314 to generate a time to frequency domain analysis of the vibration data samples. At block 1106, run frequency information is extracted from the FFT data sample results. For example, the frequency domain data is analyzed by the DSP 314 to extract the peak frequency information for further curve analysis. Control then reverts to block 1006 to determine whether sufficient data has been gathered.

Figure 12:
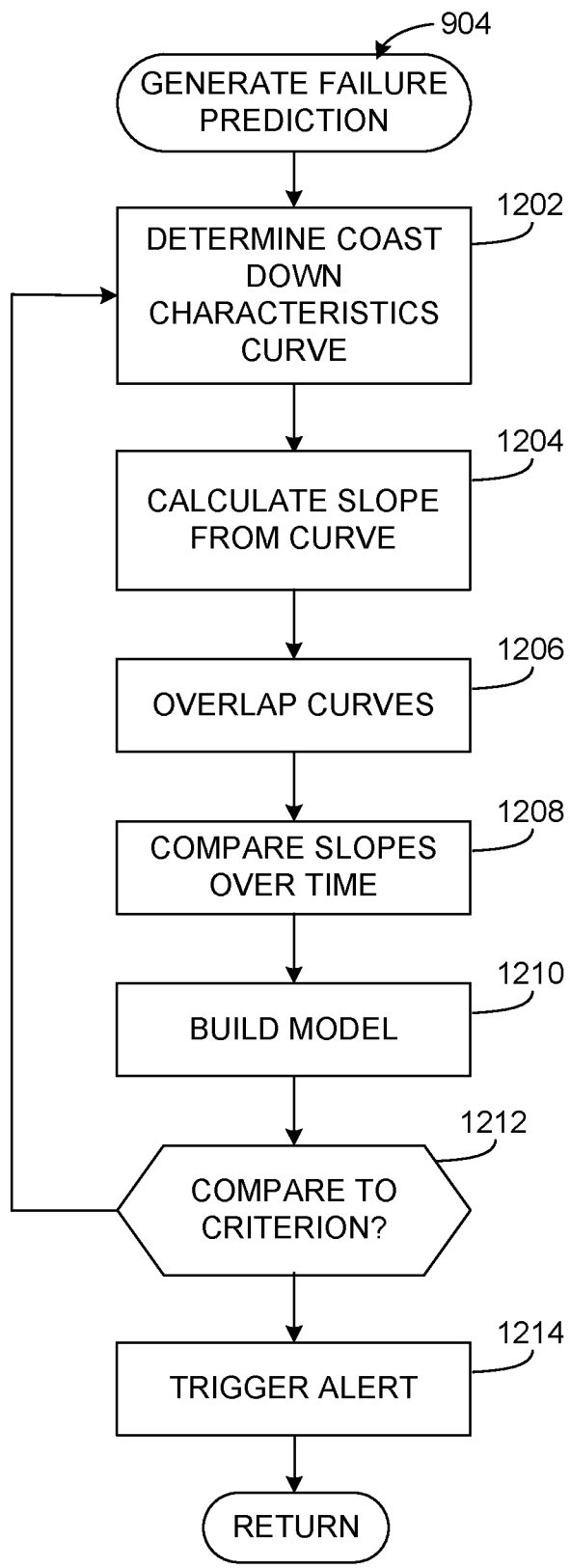

FIG. 12 illustrates further details regarding generating a failure prediction (block 904 of the example of FIG. 9). At block 1202, a coast down characteristics curve is formed from the acquired data provided to the cloud infrastructure 504 from the board 310 of the x-ray tube 300. For example, analytics software running on the predictor 506 in the cloud 504 (e.g., in conjunction with the digital twin 706, etc.) builds coast down characteristics of the x-ray tube 300 with respect to time and generates a curve to measure the slope of coast down.

Figure 13A:
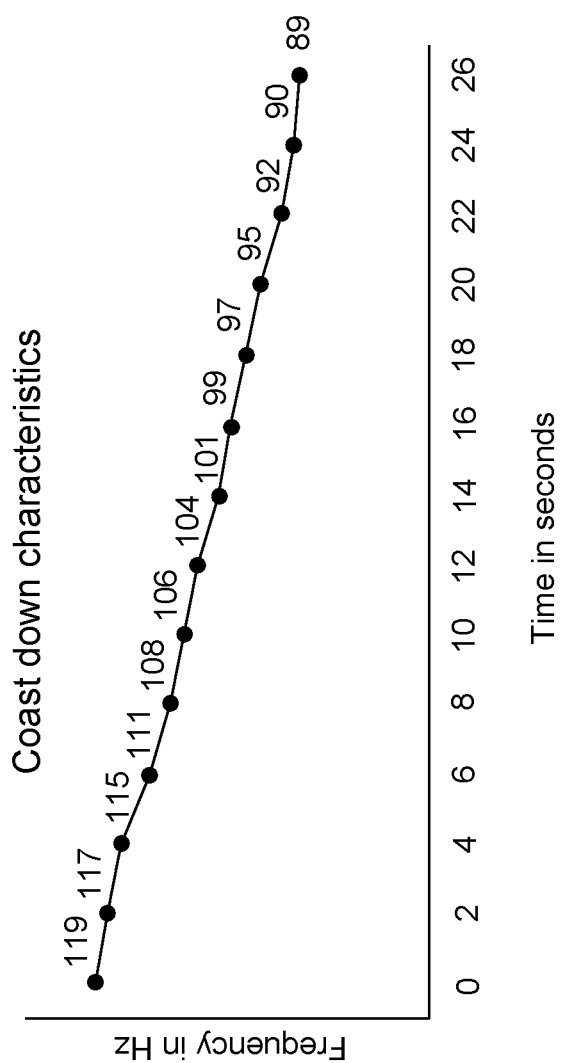
FIGS. 13A-16 depict example graphs, models, and supporting algorithms for x-ray tube coast down characterization and failure prediction.
Figure 13B:
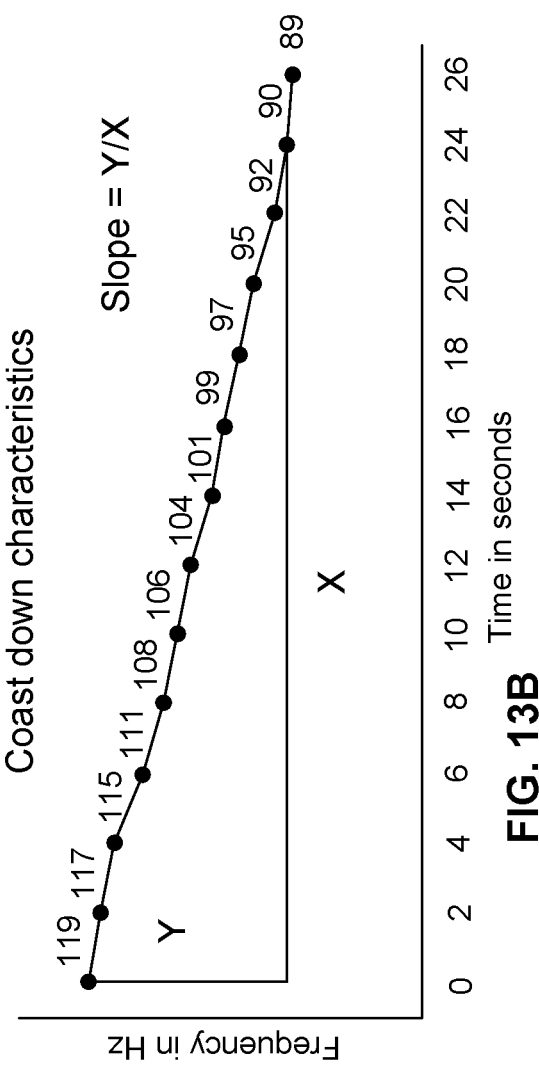
Figure 14:
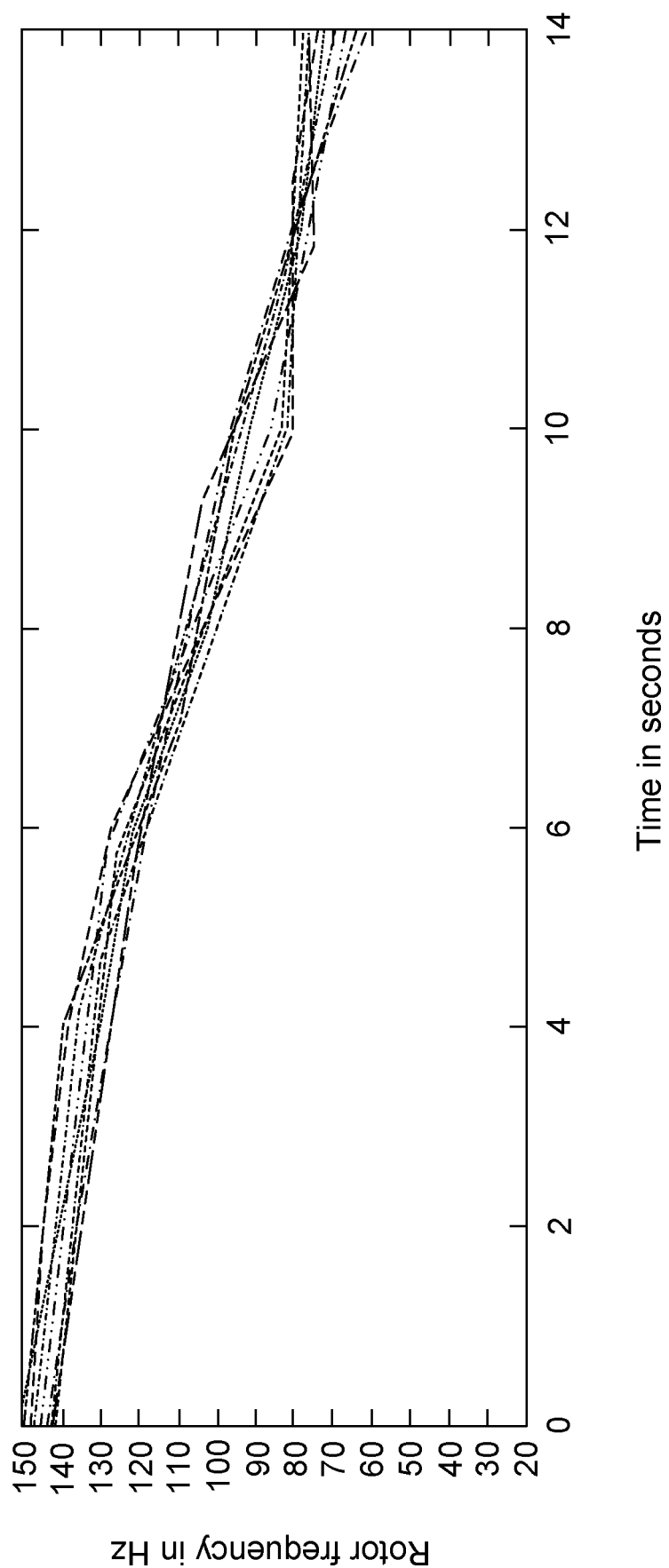

At block 1204, a slope is calculated from the coast down characteristic curve. For example, as shown in the example of FIGS. 13A-13B, a slope Y/X can be computed by comparing frequency (e.g., Y, in Hertz) over elapsed time (e.g., X, in seconds). At block 1206, computed curves are overlapped. For example, the coast down characteristic data is acquired from the board 310 for a plurality of coast down cycles 808, curves are overlapped to show how the x-ray tube 300 is performing. FIG. 14 shows an example set of overlapping curves illustrating x-ray tube rotor coast down characteristics over time by rotor frequency.

Figures 15A, 15B:
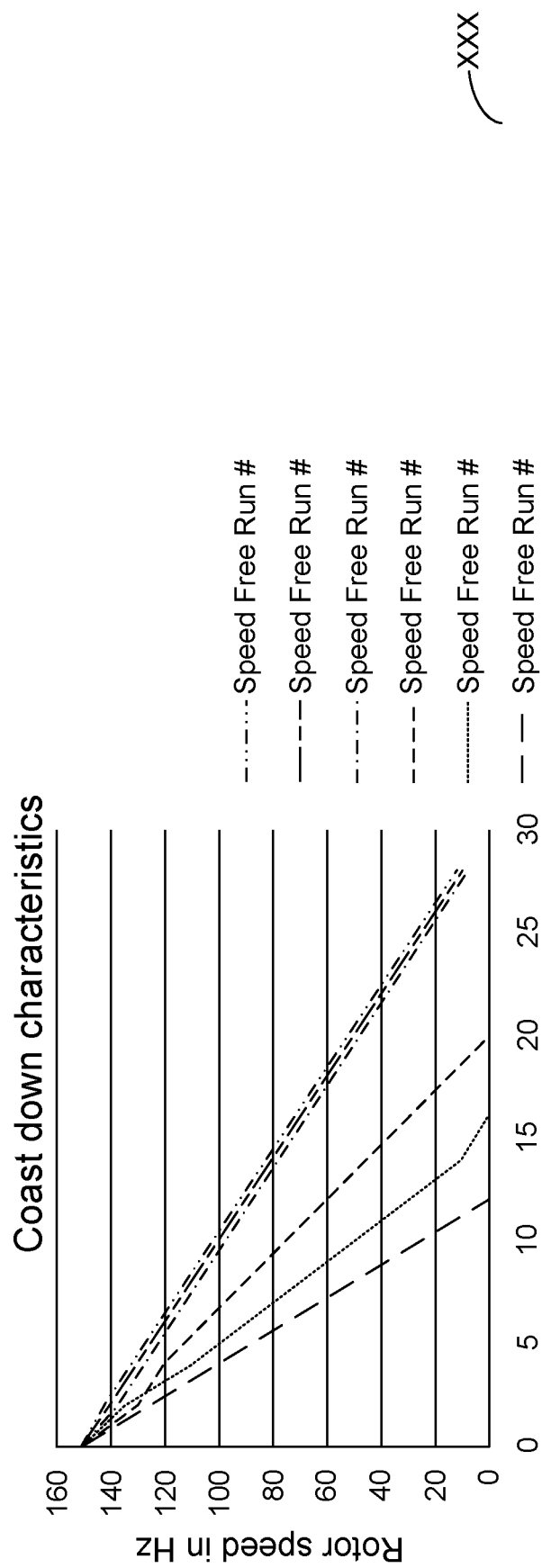
Figure 16:
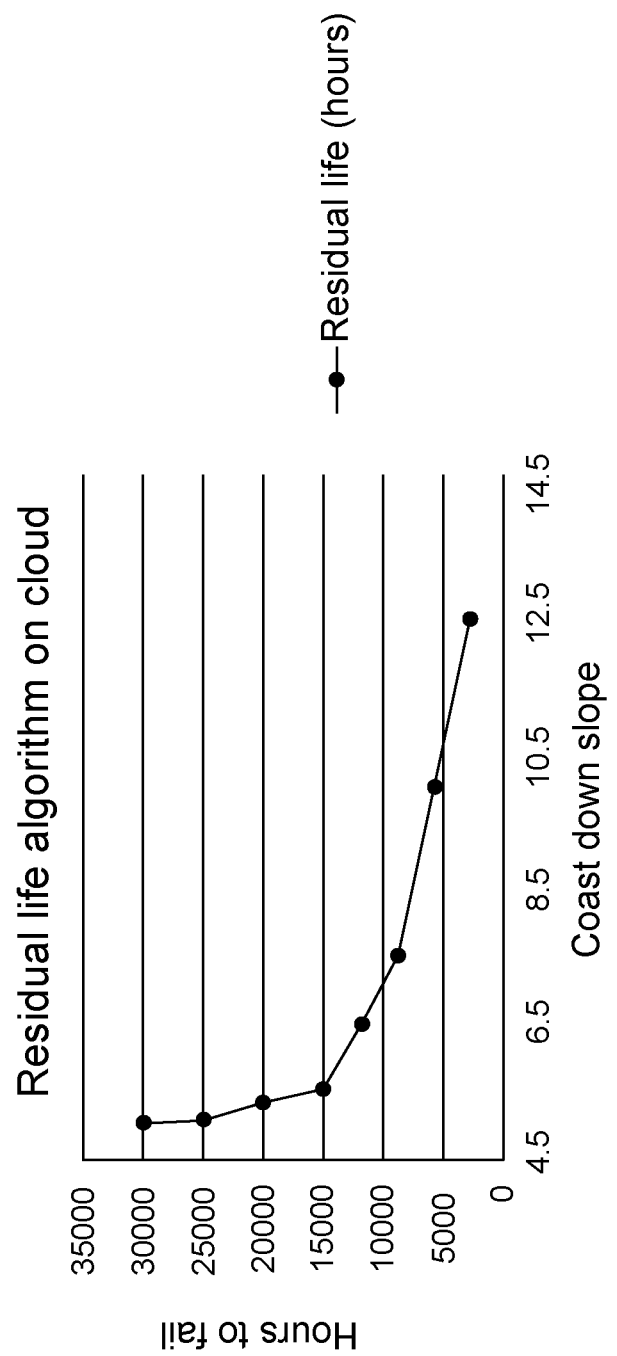

When the x-ray tube 300 is new, friction on the bearing is low and an associated coast down slope is small. That is, the time taken for the motor to coast down is very long. As the tube 300 ages, the coast down time becomes smaller, which indicates that the bearing is wearing out. At block 1208, the algorithm in the cloud 504 modeled in the digital twin 706 and applied by the predictor 506 predicts a time to fail for the x-ray tube 300 bearing by calculating the slope over a plurality of free run cycles. Thus, the slope of the curve is an indication of the friction of the bearing. The coast down characteristic is the measurement of time taken for the speed to fall from "Y1" frequency at "X1" time to "Y2" frequency at "X2" time. The slope can be calculated using a formula such as slope=(Y2−Y1)/(X2−X1) (Equation 1). As shown in the example of FIG. 15A, cost characteristics can be determined for a plurality of runs over time. At block 1210, a model (e.g., the digital twin 706) is built based on the free run curves and associated coast down characteristic slopes. For example, FIG. 15B shows an example data set forming the model based on curve and slope.

At block 1212, modeled curve slope information is analyzed in comparison to one or more criterion, such as a threshold, rate of change, etc. For example, each time a coast down curve is computed, the predictor 506 leverages an algorithm and the digital twin 706 in the cloud 504 to measure a time between slope change among a plurality of curves. The digital twin 706 enables the predictor 506 to compute a slope V/S over time by actively learning from each coast down curve. Each time a coast down is computed, residual life of the x-ray tube bearing (e.g., hours to fail, etc.) can be determined from a cumulative damage model represented by the digital twin 706. Cumulative damage models are built from the coast down slope data based on a limit, threshold, and/or other criterion set by a user, application, system, digital twin 706, etc.

At block 1214, the predictor 506 and digital twin 706 generate a prediction to indicate a potential time to fail, rate of failure, time of failure, etc., based on the digital twin's 706 cumulative damage model and the residual life determined by the predictor 506. For example, the digital twin 706 forms a learning model to evaluate a non-linear transfer function to identify a slope having a particular coast down speed with respect to time with respect to a threshold or other criterion to determine an estimate/prediction of time remaining (e.g., hours, minutes, seconds, etc.) before x-ray tube bearing failure.

Control reverts to block 906 to generate an alert based on the prediction. The alert can be generated to allow a scheduling system, repair system, user, etc., to plan downtime for x-ray tube maintenance, bearing replacement, etc., rather than unplanned, emergency repair/replacement. In certain examples, an interactive user interface provides access to prediction model/data, such as FIGS. 13A-16, as well as to schedule downtime for replacement/repair. In certain examples, a message is generated to provide a field engineer, service team, etc., with a notification to identify impending failure(s). For example, a user can configure automated messaging to notify him/her regarding x-ray tubes at a particular hospital that are estimated to fail within a certain number of days (e.g., 7 days, 10 days, 2 days, etc.). An authorized person can receive such messages to enable them to check for further information, check available replacement parts, plan for repair/replacement, etc.

Thus, certain examples use the sensor network 312, cloud computing 504, and digital twin 706 analytics to monitor the performance of the LM bearing in near real-time, and a prediction model automatically alerts users to stock, call for service, etc. Based on a more accurate prediction of repair/replace timeline, service teams can build up repair/replacement stock when needed and not maintain excess inventory when it is not likely to be used, for example.

Figure 17:
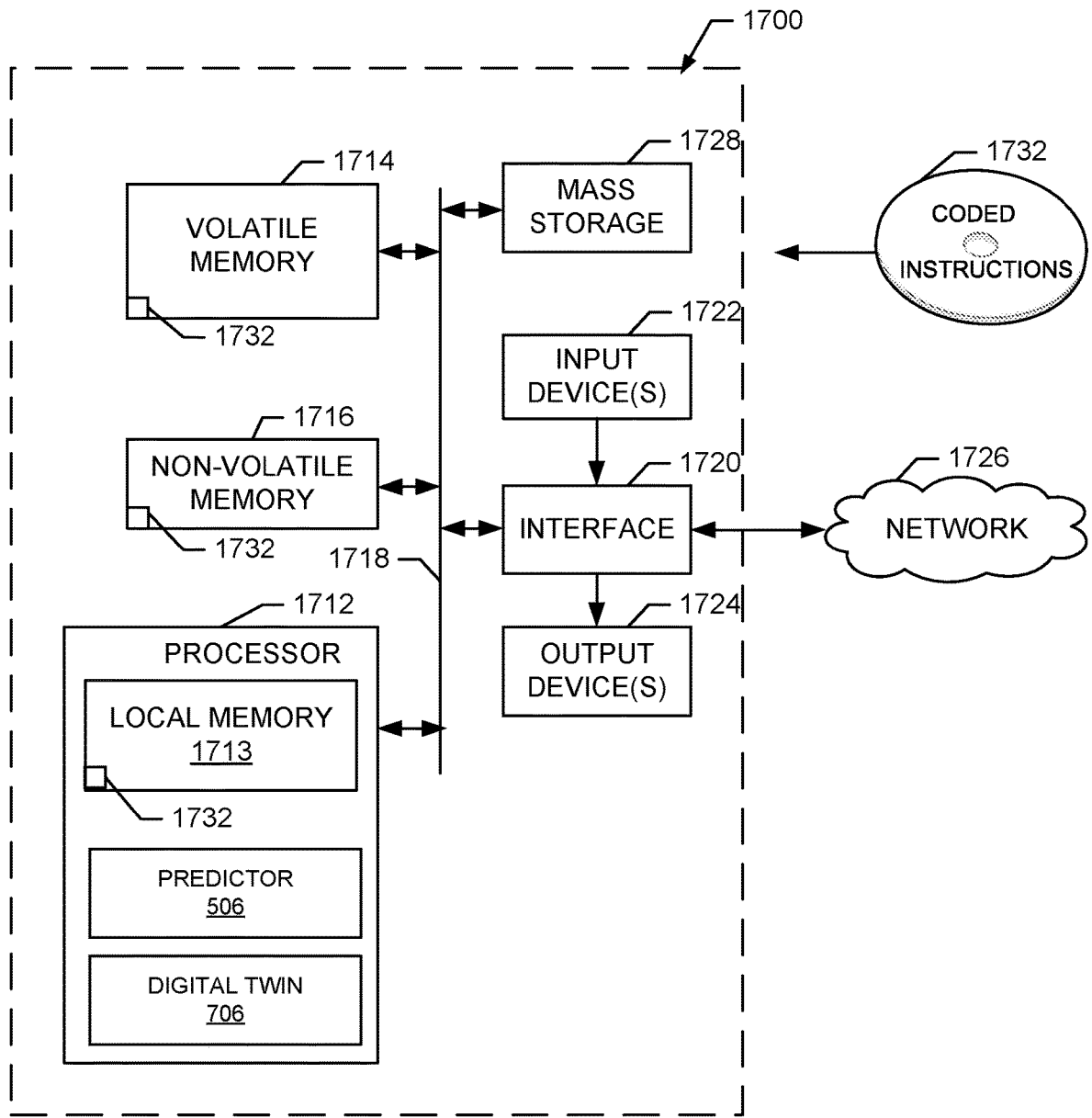
FIG. 17 is a block diagram of a processing system structured to execute the example machine readable instructions of FIGS. 9-12 to implement the example board and/or cloud infrastructure of FIGS. 1-8.

FIG. 17 is a block diagram of an example processor platform 1700 structured to executing the instructions of FIG. 17 to implement the example board 310 and/or cloud infrastructure 504 of FIGS. 3-7. The processor platform 1700 can be, for example, a server, a personal computer, a mobile device (e.g., a cell phone, a smart phone, a tablet such as an iPad™), a personal digital assistant (PDA), an Internet appliance, or any other type of computing device.

The processor platform 1700 of the illustrated example includes a processor 1712. The processor 1712 of the illustrated example is hardware. For example, the processor 1712 can be implemented by integrated circuits, logic circuits, microprocessors or controllers from any desired family or manufacturer.

In the examples, the machine readable instructions include a program for execution by one or more processors such as the processor 1712 shown in the example processor platform 1700 discussed below in connection with FIG. 17. The machine readable instructions may be stored on a tangible computer readable storage medium such as a CD-ROM, a floppy disk, a hard drive, a digital versatile disk (DVD), a Blu-ray disk, or a memory associated with the processor 1712, but the entire program and/or parts thereof could alternatively be executed by a device other than the processor 1712 and/or embodied in firmware or dedicated hardware.

The processor 1712 of the illustrated example includes a local memory 1713 (e.g., a cache). The example processor 1712 of FIG. 17 executes the instructions of FIGS. 9-12 to implement the example board 310 and/or cloud infrastructure 504.

The processor 1712 of the illustrated example is in communication with a main memory including a volatile memory 1714 and a non-volatile memory 1716 via a bus 1718. The volatile memory 1714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1716 may be implemented by flash memory and/or any other desired type of memory device. Access to the main memory 1714, 1716 is controlled by a clock controller.

The processor platform 1700 of the illustrated example also includes an interface circuit 1720. The interface circuit 1720 may be implemented by any type of interface standard, such as an Ethernet interface, a universal serial bus (USB), and/or a PCI express interface.

In the illustrated example of FIG. 17, one or more input devices 1722 are connected to the interface circuit 1720. The input device(s) 1722 permit(s) a user to enter data and commands into the processor 1712. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1724 are also connected to the interface circuit 1720 of the illustrated example. The output devices 1724 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1720 of the illustrated example, thus, typically includes a graphics driver card, a graphics driver chip or a graphics driver processor.

The interface circuit 1720 of the illustrated example also includes a communication device such as a transmitter, a receiver, a transceiver, a modem and/or network interface card to facilitate exchange of data with external machines (e.g., computing devices of any kind) via a network 1726

(e.g., an Ethernet connection, a digital subscriber line (DSL), a telephone line, coaxial cable, a cellular telephone system, etc.).

The processor platform 1700 of the illustrated example also includes one or more mass storage devices 1728 for storing software and/or data. Examples of such mass storage devices 1728 include floppy disk drives, hard drive disks, compact disk drives, Blu-ray disk drives, RAID systems, and digital versatile disk (DVD) drives.

The coded instructions 1732 of FIG. 9-12 may be stored in the mass storage device 1728, in the volatile memory 1714, in the non-volatile memory 1716, and/or on a removable tangible computer readable storage medium such as a CD or DVD.

From the foregoing, it will be appreciated that the above disclosed methods, apparatus, and articles of manufacture have been disclosed for failure detection/prediction in x-ray tube components such as bearings (e.g., LM bearings, etc.). LM bearing tubes are characterized by long service life, low noise, and expensive to buy (e.g., $50,000, etc.). The cost and complexity in manufacturing LM bearing tubes makes it difficult to produce and stock for failure replacement. This in turn increases the downtime of the hospital to get the required spare part which leads to lower customer satisfaction.

One of the biggest failure modes of an LM bearing x-ray tube is rotor LM bearing failure. There is a need to know in advance when the rotor's LM bearing in X-ray tube 300 is likely to or will fail. Certain examples enable failure prediction in advance, allowing sufficient time to order parts without maintaining excess inventory. As the failure is predicted in advance, preventive maintenance can be established with a customer to significantly reduce down time and increase customer satisfaction. The performance of the LM bearing is monitored in near real time such that engineering fixes and product updates have access to asset information and corresponding insights, which helps to evaluate the applicability of a fix with a large population size.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A circuit board device comprising:
   a sensor to detect, in a free run mode of an x-ray tube, vibration in an x-ray tube housing;
   a digital signal processor to process vibration information representing the vibration detected by the sensor to generate x-ray tube characterization information; and
   a communication interface to relay the x-ray tube characterization information to a cloud infrastructure to process the x-ray tube characterization information to generate a failure prediction based on x-ray tube bearing coast down characteristics extracted from the x-ray tube characterization information.

2. The device of claim 1, wherein the digital signal processor is to process the vibration information using a Fast Fourier Transform, and wherein the x-ray tube characterization information includes peak frequency information.

3. The device of claim 1, wherein the digital signal processor is to buffer x-ray tube characterization information until a curve is formed from data points in the x-ray tube characterization information and then the communication interface is to relay the x-ray tube characterization information to the cloud infrastructure.

4. The device of claim 1, wherein the cloud infrastructure includes a digital twin to model a cumulative damage model reflecting wear on the x-ray tube bearing.

5. The device of claim 1, wherein the cloud infrastructure is to generate a failure prediction based on x-ray tube bearing coast down characteristics extracted from the x-ray tube characterization information by determining a slope of frequency over time represented as a time for coast down speed of the x-ray tube to decrease from a frequency Y1 at a time X1 to a frequency Y2 at a time X2, the slope calculated using slope=(Y2−Y1)/(X2−X1).

6. The device of claim 1, wherein the sensor includes an accelerometer.

7. The device of claim 1, wherein the x-ray tube bearing includes a liquid metal bearing.

8. A method comprising:
   detecting, in a free run mode of an x-ray tube using a sensor, vibration in an x-ray tube housing;
   processing, using a digital signal processor, vibration information representing the vibration detected by the sensor to generate x-ray tube characterization information; and
   relaying, via a communication interface, the x-ray tube characterization information to a cloud infrastructure to process the x-ray tube characterization information to generate a failure prediction based on x-ray tube bearing coast down characteristics extracted from the x-ray tube characterization information.

9. The method of claim 8, wherein the processing the vibration information includes processing the vibration information using a Fast Fourier Transform, and wherein the x-ray tube characterization information includes peak frequency information.

10. The method of claim 8, further including buffering x-ray tube characterization information until a curve is formed from data points in the x-ray tube characterization information before relaying the x-ray tube characterization information to the cloud infrastructure.

11. The method of claim 8, further including modeling a cumulative damage model reflecting wear on the x-ray tube bearing using a digital twin to generate the failure prediction.

12. The method of claim 8, wherein the cloud infrastructure is to generate a failure prediction based on x-ray tube bearing coast down characteristics extracted from the x-ray tube characterization information by determining a slope of frequency over time represented as a time for coast down speed of the x-ray tube to decrease from a frequency Y1 at a time X1 to a frequency Y2 at a time X2, the slope calculated using slope=(Y2−Y1)/(X2−X1).

13. The method of claim 8, wherein the sensor includes an accelerometer.

14. The method of claim 8, wherein the x-ray tube bearing includes a liquid metal bearing.

15. A tangible computer readable storage medium comprising instructions which, when executed, cause a machine to at least:
   receive, from a circuit board on an x-ray tube, x-ray tube characterization information generated from vibration information detected by a sensor from an x-ray tube housing, the x-ray tube characterization information related to bearing vibration in the x-ray tube;
   process, using a processor, the x-ray tube characterization information based on x-ray tube bearing coast down characteristics extracted from the x-ray tube characterization information to identify at least one of a rate of failure or a time to failure;

generate, using the processor, a failure prediction based on the at least one of a rate of failure or a time to failure; and trigger, using the processor an alert based on the failure prediction.

16. The computer readable storage medium of claim 15, wherein the x-ray tube characterization information is obtained by processing vibration information detected from the x-ray tube using a Fast Fourier Transform, and wherein the x-ray tube characterization information includes peak frequency information.

17. The computer readable storage medium of claim 15, wherein the instructions, when executed, form a curve from data points in the x-ray tube characterization information, overlay a plurality of curves, and analyze slope information to generate the failure prediction.

18. The computer readable storage medium of claim 15, wherein the instructions, when executed, form a digital twin to model a cumulative damage model reflecting wear on the x-ray tube bearing.

19. The computer readable storage medium of claim 15, wherein the failure prediction is generated based on x-ray tube bearing coast down characteristics extracted from the x-ray tube characterization information by determining a slope of frequency over time represented as a time for coast down speed of the x-ray tube to decrease from a frequency Y1 at a time X1 to a frequency Y2 at a time X2, the slope calculated using slope=(Y2−Y1)/(X2−X1).

20. The computer readable storage medium of claim 15, wherein the alert includes a message triggering an interactive interface to schedule at least one of repair or replacement of the x-ray tube.

* * * * *